United States Patent [19]
Kishi et al.

[11] Patent Number: 6,114,134
[45] Date of Patent: Sep. 5, 2000

[54] METHOD FOR ASSAYING BIOLOGICAL SPECIMENS FOR SUBSTANCES CONTAINED IN THE COMPONENTS THEREOF AND REAGENT TO BE USED IN THIS METHOD

[75] Inventors: Koji Kishi; Tsutomu Kakuyama; Yasushi Shirahase; Yoshifumi Watazu, all of Hyogo, Japan

[73] Assignee: International Reagents Corporation, Hyogo, Japan

[21] Appl. No.: 09/453,474

[22] Filed: Dec. 2, 1999

Related U.S. Application Data

[63] Continuation of application No. PCT/JP98/02795, Jun. 22, 1998.

[30] Foreign Application Priority Data

Jun. 25, 1997 [JP] Japan ..................................... 9-169281

[51] Int. Cl.[7] ................. C12Q 1/60; C12Q 1/00
[52] U.S. Cl. ................. 435/11; 435/975; 435/4; 435/19; 435/23; 435/20; 435/26
[58] Field of Search ................. 435/11, 4, 975, 435/19, 23, 20, 26

[56] References Cited

U.S. PATENT DOCUMENTS 5,409,959   4/1995   Hwang et al. ........................ 514/732

FOREIGN PATENT DOCUMENTS

| | | |
|---|---|---|
| 1-503596A | 7/1989 | Japan . |
| 6-242110A | 2/1994 | Japan . |
| 8-503937A | 4/1996 | Japan . |
| 8-131197A | 5/1996 | Japan . |

*Primary Examiner*—Louise N. Leary
*Attorney, Agent, or Firm*—Sughrue, Mion, Zinn, Macpeak & Seas, PLLC

[57] ABSTRACT

A method for assaying biological specimens for substances contained in the components of each specimen by the use of one or more kinds of calixarenes; and a reagent comprising one or more kinds of calixarenes. The method utilizes complexes formed by calixarenes and the components of biological specimens, and makes it possible to assay biological specimens for substances contained in the components of each specimen, for example, for cholesterol contained in high-density lipoprotein (HDL), without preliminary separation from the other components of the biological specimen. The method can be conducted by easy and simple operations and lessen measurement errors or problems caused by man, and permits continuous measurement with general-purpose automatic analyzing apparatuses and multi-channel measurement together with other test items.

10 Claims, No Drawings

METHOD FOR ASSAYING BIOLOGICAL SPECIMENS FOR SUBSTANCES CONTAINED IN THE COMPONENTS THEREOF AND REAGENT TO BE USED IN THIS METHOD

RELATIONSHIP TO OTHER APPLICATIONS

This application is a continuation application of PCT/JP98/02795 filed Jun. 22, 1998, the whole contents of which is incorporated herein by reference.

TECHNICAL FIELD

The present invention relates to a method for assaying biological specimens for substances contained in the components of each specimen in the field of clinical diagnosis and to a reagent for use therein. More specifically, the present invention relates to a method for assaying high density lipoprotein (HDL) for cholesterol and to a reagent for use therein.

BACKGROUND ART

Lipoproteins have from since been fractionated by ultra-centrifugation operation into high density lipoprotein (HDL, density: 1.063–1.21), low density lipoprotein (LDL, density: 1.019–1.063), very low density lipoprotein (VLDL, density: 1.006–1.019), and chylomicron (CM, density<1.006). The fractionation operation needs an ultracentrifuge and in addition must continue centrifugation for several days so that it is impossible to treat many samples.

In place of this, a method has become the main current in which by mixing serum with a solution which comprises a precipitation agent that contains both a polyethylene glycol or a polyanion such as dextransulfate and a divalent cation such as calcium, or both phosphorous tungstic acid and a divalent cation, LDL, VLDL, and CM are precipitated and only HDL that remains in the supernatant after the centrifugation is fractionated. In this method, use can be made of an automatic analyzing apparatus which has widely prevailed in the field of clinical assays. That is, since the assay of total cholesterol using an enzyme assay method has been established by use of an automatic analyzing apparatus, utilization of the established assay method has enabled the measurement of concentration of cholesterol in the fractionated HDL.

However, this method still needs centrifugation operation though at a low speed and there has been the problem of artificial errors in quantitative determination or misplacement of samples when the precipitation agent and serum are mixed with each other. In addition, it has been impossible to measure other general biochemical items simultaneously by use of an automatic analyzing apparatus. Clinical assays are demanded to be carried out speedily, which also give rise to the desire for a shortening of test time.

On the other hand, from clinical point of view, there has been a report which lays importance on the level of cholesterol in LDL, which is a risk factor for arteriosclerosis ("Standard Level of Total Cholesterol and Basis for Its Setting", Domyaku Koka (Arteriosclerosis), 24 (6), 260 (1966)). Currently, the level of cholesterol in LDL is obtained from measured values of total cholesterol (T-CHO), neutral fats (TG) and cholesterol in HDL according to an equation by introducing an empirical factor therein. The equation (Friedewald W. T., et al., Clin. Chem., 18, 499–502 (1972)) is as shown below;

Cholesterol value in LDL=(T-CHO value)−(Cholesterol value in HDL)−(TG value)/5.

In this method, all the three terms to be measured must be exactly measured before the equation can be valid. It is said that the calculated value does not reflect the concentration of cholesterol in LDL when TG value exceeds 400 mg/dl or the concentration of cholesterol in LDL is 100 mg/dl or less (Warnick G. R., et al., Clin. Chem., 36(1), 15–19 (1990), McNamara, J. R., et al., Clin. Chem., 36(1), 36–42 (1990)) Therefore, extraordinary values which are the target of assay cannot be attained by this method. Besides, there have been a method in which lipoprotein is isolated by electrophoresis and the quantity of protein is measured or a method in which cholesterol is measured for respective lipoproteins by HPLC. However, both of them are deficient in the ability to treat many samples and need an expensive apparatus.

Recently, in order to dissolve the above-described problems associated with the measurement of cholesterol in HDL, an automatic kit for the measurement of cholesterol in HDL has been developed and prevailing. However, the technologies described in the Japanese Registered Patent No. 2600065, Japanese Patent Application Laid-open No. Hei 8-201393 and Japanese Patent Application Laid-open No. Hei 8-31195 use a precipitation agent in combination and the metal used as a divalent cation contained in the precipitation agent forms insoluble precipitation by the action of a detergent generally used in an automatic analyzing apparatus, and the precipitation accumulates in a waste disposal mechanism, which causes a disorder of the automatic analyzing apparatus. Further, insoluble agglutinates are formed in the reaction mixture and the agglutinates not only make the reaction mixture turbid, which could affect the results of measurement, and cause an error in measurement, but also stain the reaction cell to give not a small influence on the results of measurement of other biochemical items simultaneously measured.

In most automatic analyzing apparatus now prevailing, the reaction is often completed in 10 minutes. In this case, the occurrence of a change in turbidity, if any, casts a question on the accuracy of the measured values. In addition, the problem also arises that the turbidity of reaction mixture deteriorates reproducibility. Therefore, samples which can be measured in the apparatus are limited and a wide range of measuring wavelengths and various types of samples from patients cannot be served. For example, it has the defect that in the vicinity of 340 nm (UV region), the absorbance is 2 or more, or 3 or more and frequently exceeds the tolerance limits of the analyzing apparatus, due to the turbidity caused by the agglutinates.

The technology described in Japanese Patent Application Laid-open No. Hei 9-96637, which uses a divalent cation, is a method involving use of an antiserum contained in the reaction mixture which forms agglutinates with a lipoprotein. This also forms insoluble antigen-antibody agglutinates so that the reaction cell is stained. Therefore, no small an influence is given on the results of measurement of other biochemical items that are measured simultaneously. Furthermore, the high turbidity in the reaction mixture makes accurate measurement impossible for the cholesterol in HDL in particular in UV region because of the same causes as described above. In a longer wavelength region, the measured values are inaccurate due to the influence of turbidity.

On the other hand, in the case of measurement of cholesterol in LDL, it is a current status that a calculation method has to be taken.

An object of the present invention is to provide a method for assaying biological specimens for substances contained in the components of each specimen, such as cholesterol in HDL or LDL, etc., by use of a general-purpose automatic analyzing apparatus, without separation of the specimen by centrifugation operation and to provide a reagent for use therein.

DISCLOSURE OF THE INVENTION

The present inventors have made intensive study with view to solving the above-described problems and as a result they have found that calixarenes, which have been developed for inclusion of metal, etc. (Rogers, R. D., et al., J. Radioanal. Nucl. Chem., 208, 153–161 (1996)), can form a complex selectively with a specified substance in the components contained in biological specimens, for example, cholesterol in a lipoprotein, so that they are useful for fractional quantitative determination of the substance in the components without separation operations.

That is, the present invention relates to a reagent comprising calixarenes, to a reagent containing calixarenes for assaying components in biological specimens for substances, and to a method for assaying biological specimens for substances contained in the components thereof by use of calixarenes characterized in that one or more of the calixarenes form a complex with a component or components in a biological specimen.

The components in a biological specimen mean specified components contained in serum or plasma, for example, lipoproteins such as HDL, LDL, VLDL, CM, and remnant-like particle. The substances in the components in each specimen mean substances contained in the components in the biological specimens that are the target of analysis, for example, cholesterol, neutral fats, phospholipids, etc., when the component in the biological specimens are lipoproteins.

Calixarenes, which are constituted of the unit of phenol, comprise a cyclic oligomer of 4 to 8 phenol molecules bonded one to another through a methylene group to form a ring. Calixarenes include calix(4)arene, calix(6)arene, calix(8)arene, calix(4)arene sulfate, calix(6)arene sulfate, calix(8)arene sulfate, calix(4)arene acetate, calix(6)arene acetate, calix(8)arene acetate, carboxycalix(4)arene, carboxycalix(6)arene, carboxycalix(8)arene, calix(4)areneamine, calix(6)areneamine, calix(8)areneamine, etc. In the present invention, one or more kinds selected from these calixarenes can be used and upon use no limitation is posed. Calixarene sulfate, which has been successfully commercialized, is excellent in water solubility so that it is easy to handle. When the calixarenes are applied to the measurement of cholesterol, they may be added in the reaction mixture in an amount of 0.05 to 20 mmol/l, preferably 0.1 to 5 mmol/l, under the conditions where cholesterol can be measured enzymatically.

The assay in the present invention means measurement of the substances in the components in biological specimens, and to determine them by quality or by quantity.

That calixarenes form complexes with components in a biological specimen means that calixarenes bind with components in a biological specimen and the manner of binding is not limited particularly so far as the calixarenes bind with the components in the biological specimen and it includes, for example, ionic bonding, coordination bonding, etc.

Lipoproteins include a lipid inside and a protein outside as a result of binding of a lipid component containing cholesterol with an apoprotein and are solubilized in a living organism. Calixarenes form complexes mainly with LDL or VLDL through ionic bonding on the surface of the lipoprotein to inhibit the release of substances constituting the lipoprotein components (for example, cholesterol). Therefore, the formation of a complex means the inhibition of an enzyme reaction of a substance contained in the components in the biological specimens in which the complex is formed and this enables the measurement of the target substance in the components in the biological specimens by an enzyme reaction. For example, the cholesterol or neutral fats in HDL can be determined by inhibiting the enzyme reaction of cholesterol or neutral fats in LDL and VLDL.

The pH conditions of reaction mixture depend on the substance to be assayed and when the cholesterol in HDL, for example, is to be measured, may be those conditions under which the measurement of total cholesterol is completed, usually in the range of pH 6.0 to 9.0.

In the present invention, the component in biological specimens as a target of assay can be selected by changing the concentration of calixarenes, pH, surfactant, origin of enzyme, or the order of reaction with enzyme and respective conditions can be determined by experiments. One skilled in the art can readily practice such an optimization of conditions.

Thus, that the components in biological specimens containing substances as a target for measurement can be selected by changing the concentrations of calixarenes is useful in their application in the field of extracorporeal diagnostic medicaments. For example, in the conventional methods, the measurement of cholesterol in HDL was carried out by use of a method limited to the measurement of only the substance that is the target of measurement (cholesterol) and the method cannot be applied to the measurement of substances other than the cholesterol in the same HDL, for example, the neutral fats in HDL. In the measurement of the same cholesterol, the method is effective only for the cholesterol in HDL and is not applicable to other lipoproteins, for example, the cholesterol in LDL. The present invention is characterized in that it can be applied to the assay of different substances contained in the same component in the biological specimen. For example, it can be applied to the assay of not only the cholesterol in HDL but also of the neutral fats or phospholipids in HDL. Therefore, the cholesterol, neutral fats and phospholipids contained in HDL, LDL, VLDL, CM, and lipoprotein fractions of remnant-like particle can be made to be the targets of measurement.

The reagent of the present invention is provided usually as a reagent kit in which calixarenes are blended with a known reagent for measurement suitable for the measurement of substances in the components in biological specimens such that the final concentrations of calixarenes are desired concentrations, or as a reagent kit in which a reagent containing calixarenes adjusted to desired concentrations is combined with a known reagent for measurement. The form of reagent provided may be in a dry state or in a liquid state and is not limited particularly. The reagent kit may be blended with activators for enzymes. The reagent kit may contain a combination of different kinds of reagents which differ in the timing of addition in the reaction mixture, for example, a combination of a reagent for a first reaction and a reagent for a second reaction.

The method of assay according to the present invention includes a mode in which calixarenes are added such that their final concentrations are desired concentrations upon preparation by adding a buffer solution to various commercially available reagents for measurement.

The reagent of the present invention is prepared appropriately so as to contain calixarenes and reagents such as enzymes which react with the target substances in the components in biological specimens as the other components. For example, the level of cholesterol in HDL or LDL can be measured by the method for measuring total cholesterol. In this case, use is made of one or more kinds of enzymes selected from the group consisting of lipoprotein lipase (LIP), cholesterol esterase (CE), cholesterol dehydrogenase (CDH, for example, nicotinamide adenine dinucleotide dependent cholesterol dehydrogenase, nicotinamide adenine dinucleotide phosphate dependent cholesterol dehydrogenase, etc.) and cholesterol oxidase (CO). Furthermore, appropriate selection is made of activators, stabilizers, coenzymes, peroxidase (PO) for the measurement of hydrogen peroxide, and colorants which are added under the conditions for completing the reaction for the measurement of cholesterol.

When CDH is used, a technology of adding hydrazines for the purpose of inhibiting a reverse reaction of the enzyme has previously been reported (Japanese Patent Application Laid-open No. Hei 5-176797). Also, in the present invention, assays can be carried out under the conditions under which hydrazines are added. There is the technology of chemically modifying enzymes so that the enzymes can have selectivity (Japanese Registered Patent No. 2600065). In the present invention, such enzymes can be used. However, in the present invention, sufficient selectivity can be obtained without using such enzymes.

Coenzymes used in the case where CDH is used include $\beta$-nicotinamide adenine dinucleotide, oxidation form (NAD), Thio-nicotinamide adenine dinucleotide, oxidation form (t-NAD), $\beta$-nicotinamide adenine dinucleotide phosphate, oxidation form (NADP), Thio-nicotinamide adenine dinucleotide phosphate, oxidation form (t-NADP), etc. and one or more coenzymes selected from the group consisting of these are used. In the presence of cholesterol, these coenzymes are converted into respective reduction forms, i.e., NADH, t-NADH, NADPH, and t-NADPH.

The cholates and detergents used as an activator for enzymes in the measurement of total cholesterol may be selected appropriately under the conditions under which cholesterol is measured with enzymes and used after adjusting the concentration by experiment. For example, in the case where the cholesterol in HDL is to be measured, in a first reaction, calixarenes may be added to lipoproteins other than HDL to form a complex for stabilization, and in a second reaction, an enzyme, etc. may be added to measure the concentration of the cholesterol in HDL.

In the case where the cholesterol in LDL is to be measured, a combination of the conditions previously described is used and a complex with LDL is formed for stabilization in a first reaction while the cholesterols in HDL and VLDL are eliminated by preliminary reaction and the remaining cholesterol in LDL is measured in a second reaction.

The combinations and concentrations of calixarenes which form complexes with lipoproteins in the first reaction may be adjusted. In the measurement of cholesterol, enzyme reactions using 3 types of enzyme (1) CDH, (2) COD and LIP, and (3) CE in combination may be used. In the second reaction, detergents, cholates, enzymes, etc. for decomposing the LDL complex are added and measurement is made of the cholesterol in LDL which is not reacted in the first reaction, then the concentration of the cholesterol in LDL can be obtained by a deduction from the concentration of cholesterol in the first reaction. The compounds added in order to decompose LDL are not limited particularly so long as they do not interfere with the enzymatic measurement of cholesterol.

In the case where the cholesterol in VLDL is to be measured, a combination of the conditions previously described is used and a complex with VLDL is formed for stabilization in a first reaction while the cholesterols in HDL and LDL are measured preliminarily. In the first reaction, the combinations and concentrations of calixarenes which form complexes with lipoproteins may be adjusted appropriately. In the second reaction, detergents, cholates, enzymes, etc. which decompose the VLDL complex are added and measurement is made of the cholesterol in VLDL which is not reacted in the first reaction. Then the concentration of the cholesterol in VLDL can be obtained by a deduction from the concentration of cholesterol in the first reaction. In this case, the compounds added in order to decompose VLDL are not limited particularly so long as they do not interfere with the enzymatic measurement of cholesterol.

The method which involves the formation of a complex and measurement of the target substance by an enzyme reaction is applicable not only to selective measurement of cholesterol in lipoproteins but also to measurement of neutral fats or phospholipids for respective lipoproteins by appropriately changing the enzyme corresponding to the target substance.

Hereafter, the present invention will be described in detail by examples of measurement of cholesterols in HDL and LDL. However, the present invention is not limited thereto.

EXAMPLE 1

The following reagents 1 and 2 were prepared and HDL-cholesterol was measured.

Preparation of Reagent 1

| | |
|---|---|
| Buffer solution | pH 6.5 |
| Calix(6)arene sulfate | 1.0 mmol/l |
| Hydrazinium dichloride | 100 mmol/l |
| $\beta$-nicotinamide adenine dinucleotide, oxidation form (NAD) | 5.0 mmol/l |

Preparation of Reagent 2

| | |
|---|---|
| Buffer solution | pH 8.5 |
| Cholesterol dehydrogenase | 20.0 U/ml |
| Cholesterol esterase | 6.0 U/ml |

As samples were used 25 serum samples from ordinary persons. Measurement was practiced using an automatic analyzing apparatus (Hitachi 7170 Type Automatic Analyzing Apparatus). The operation was made by first adding 180 $\mu$l of Reagent 1 to 5 $\mu$l of each sample and incubating each mixture at 37° C. for 5 minutes and at this point in time Absorbance 1 was measured at a main wavelength of 340 nm and a sub wavelength of 570 nm.

Further, 60 $\mu$l of Reagent 2 was added to each sample and the resulting mixtures were incubated at 37° C. for 5 minutes and at this point in time Absorbance 2 was measured at a main wavelength of 340 nm and at a sub wavelength of 570 nm. A difference between Absorbance 1 and Absorbance 2 was obtained and the value of sample was calculated based on the control of a known HDL-cholesterol concentration as a standard solution. As a control method, the polyethylene glycol (PG) method was used. The PG method was carried out using PG POL manufactured by International Reagents Corporation. The concentration of cholesterol in the supernatant after centrifugation was obtained by use of T-CHO Reagent A manufactured by International Reagents Corporation. The results obtained are shown in Table 1.

Correlation with the control method was as follows: correlation coefficient: 0.993, regression equation: $Y=0.989X+1.18$, thus giving a good correlation. Note that Y in the regression equation is the value based on Example 1 (unit: mg/dl) and X is the value obtained by the PG method (unit: mg/dl).

TABLE 1

Results of Measurements (Unit: mg/dl)

| Sample No. | Method of Invention | Control Method |
| --- | --- | --- |
| 1 | 39.2 | 42.2 |
| 2 | 45.5 | 43.2 |
| 3 | 57.7 | 56.4 |
| 4 | 47.2 | 46.2 |
| 5 | 75.4 | 74.4 |
| 6 | 41.9 | 39.9 |
| 7 | 37.4 | 36.6 |
| 8 | 94.3 | 88.5 |
| 9 | 50.1 | 49.3 |
| 10 | 85.9 | 91.7 |
| 11 | 95.1 | 92.6 |
| 12 | 39.1 | 39.5 |
| 13 | 29.7 | 28.0 |
| 14 | 61.8 | 62.1 |
| 15 | 52.5 | 51.0 |
| 16 | 63.6 | 61.9 |
| 17 | 69.6 | 71.0 |
| 18 | 81.4 | 79.9 |
| 19 | 27.0 | 25.0 |
| 20 | 50.0 | 50.5 |
| 21 | 40.4 | 39.5 |
| 22 | 74.9 | 77.0 |
| 23 | 69.2 | 67.2 |
| 24 | 52.8 | 54.1 |
| 25 | 68.8 | 68.6 |

EXAMPLE 2

The following reagents 1 and 2 were prepared and HDL-cholesterol was measured.

Preparation Reagent 1

| | |
| --- | --- |
| Buffer solution | pH 6.5 |
| Sodium N-(2-hydroxy-3-sulfopropyl)-3,5-dimethoxy-aniline | 1.0 mmol/l |
| Calix(6)arene sulfate | 1.0 mmol/l |
| Peroxidase | 5.0 U/l |

Preparation of Reagent 2

| | |
| --- | --- |
| Buffer solution | pH 7.0 |
| Cholesterol oxidase | 10.0 U/ml |
| Cholesterol esterase | 6.0 U/ml |
| 4-Aminoantipyrine | 10.0 mmol/l |

As samples were used 20 serum samples from ordinary persons. Measurement was practiced using an automatic analyzing apparatus (Hitachi 7170 Type Automatic Analyzing Apparatus). The operation was made by first adding 180 µl of Reagent 1 to 3 µl of each sample and incubating each mixture at 37° C. for 5 minutes and at this point in time Absorbance 1 was measured at a main wavelength of 600 nm and a sub wavelength of 700 nm.

Further, 60 µl of Reagent 2 was added to each sample and the resulting mixtures were incubated at 37° C. for 5 minutes and at this point in time Absorbance 2 was measured at a main wavelength of 600 nm and at a sub wavelength of 700 nm. A difference between Absorbance 1 and Absorbance 2 was obtained and the value of sample was calculated based on the control of a known HDL-cholesterol concentration as a standard solution. As a control method, the polyethylene glycol (PG) method was used. The PG method was carried out in the same manner as in Example 1. The results obtained are shown in Table 2.

Correlation with the control method was as follows: correlation coefficient: 0.986, regression equation: $Y=0.879X+6.03$, thus giving a good correlation. Note that Y in the regression equation is the value based on Example 2 (unit: mg/dl) and X is the value obtained by the PG method (unit: mg/dl).

TABLE 2

Results of Measurements (Unit: mg/dl)

| Sample No. | Method of Invention | Control Method |
| --- | --- | --- |
| 1 | 49.2 | 50.9 |
| 2 | 43.9 | 45.4 |
| 3 | 51.9 | 58.0 |
| 4 | 51.0 | 51.9 |
| 5 | 66.9 | 71.4 |
| 6 | 70.4 | 71.1 |
| 7 | 47.6 | 43.3 |
| 8 | 28.1 | 25.0 |
| 9 | 34.8 | 32.4 |
| 10 | 69.7 | 73.3 |
| 11 | 41.7 | 41.5 |
| 12 | 60.8 | 62.0 |
| 13 | 102.1 | 104.3 |
| 14 | 42.5 | 47.2 |
| 15 | 47.1 | 45.9 |
| 16 | 63.6 | 67.3 |
| 17 | 45.6 | 42.8 |
| 18 | 42.3 | 37.6 |
| 19 | 52.5 | 54.9 |
| 20 | 37.0 | 30.1 |

EXAMPLE 3

The following reagents 1 and 2 were prepared and LDL-cholesterol was measured.

Preparation of Reagent 1

| | |
| --- | --- |
| Buffer solution | pH 7.5 |
| Calix(6)arene sulfate | 0.8 mmol/l |
| Hydrazinium dichloride | 100 mmol/l |
| β-nicotinamide adenine dinucleotide, oxidation form (NAD) | 5.0 mmol/l |
| Cholesterol dehydrogenase | 10.0 U/ml |
| Cholesterol esterase | 4.0 U/ml |

Preparation of Reagent 2

| Buffer solution | pH 7.5 |
|---|---|
| Cholesterol esterase | 3.0 U/ml |

As samples were used 24 serum samples from ordinary persons and values of samples were calculated using as a standard solution the control of a known LDL-cholesterol concentration whose conversion is known in accordance with the Friedewald formula. Measurement was practiced using an automatic analyzing apparatus (Hitachi 7170 Type Automatic Analyzing Apparatus). The operation was made by first adding 210 µl of Reagent 1 to 3 µl of each sample and incubating each mixture at 37° C. for 5 minutes and at this point in time Absorbance 1 was measured at a main wavelength of 340 nm and a sub wavelength of 570 nm.

Further, 70 µl of Reagent 2 was added to each sample and the resulting mixtures were incubated at 37° C. for 5 minutes and at this point in time Absorbance 2 was measured at a main wavelength of 340 nm and at a sub wavelength of 570 nm. A difference between Absorbance 1 and Absorbance 2 was obtained and the value of sample (unit: mg/dl) was calculated based on the control of a known LDL-cholesterol concentration as the standard solution.

As a control method, use is made of T-CHO Reagent KL "KOKUSAI" and TG Reagent A, both manufactured by International Reagents Corporation, and PG POL method and the concentration of LDL-cholesterol was obtained in accordance with the Friedewald formula. The results obtained are shown in Table 3.

Correlation with the control method was as follows: correlation coefficient: 0.982, regression equation: Y=1.008X+5.98, thus giving a good correlation. Note that Y in the regression equation is the value based on Example 3 (unit: mg/dl) and X is the value obtained by the control method (unit: mg/dl).

TABLE 3

Results of Measurements (Unit: mg/dl)

| Sample No. | Method of Invention | Control Method |
|---|---|---|
| 1 | 49.8 | 60.8 |
| 2 | 121.0 | 120.7 |
| 3 | 144.8 | 144.8 |
| 4 | 85.9 | 88.9 |
| 5 | 70.3 | 60.8 |
| 6 | 93.1 | 81.1 |
| 7 | 105.5 | 92.1 |
| 8 | 116.0 | 103.1 |
| 9 | 130.0 | 108.2 |
| 10 | 129.7 | 116.2 |
| 11 | 139.2 | 126.5 |
| 12 | 154.3 | 138.7 |
| 13 | 160.9 | 151.3 |
| 14 | 189.7 | 173.0 |
| 15 | 243.5 | 236.9 |
| 16 | 77.5 | 79.3 |
| 17 | 165.5 | 173.9 |
| 18 | 168.3 | 170.3 |
| 19 | 121.6 | 118.2 |
| 20 | 93.6 | 87.3 |
| 21 | 99.0 | 92.7 |
| 22 | 70.7 | 63.8 |
| 23 | 175.7 | 164.0 |
| 24 | 112.2 | 99.3 |

INDUSTRIAL APPLICABILITY

According to the present invention, substances in the components in biological specimens, for example, a substance (cholesterol, etc.) in a specified fraction in serum (liprotein, etc.) can be assayed without separation from any other fractions. Therefore, since separation by fractionation such as centrifugation fractionation is unnecessary, the method of the present invention is easy in operation so that errors in measurement and artificially caused problems can be decreased.

Furthermore, the method of the present invention can be applied to methods using two kinds of reagents so that continuous measurement using a general-purpose automatic analyzing apparatus is possible, which enables multi-channel measurement in combination with other test items.

The present application is based on Japanese Patent Application No. Hei 9-169281 filed in Japan, the whole contents of which application is incorporated herein by reference.

What is claimed is:

1. In a method for fractional measurement of a constituent substance of a lipoprotein in components in biological specimens, the step to fractionally mask enzyme reactivity of the constituent substance in a specified lipoprotein, characterized in that calixarenes are caused to form complexes with the specified lipoprotein.

2. In a method for fractional measurement of a constituent substance of a lipoprotein in components in biological specimens, the step to fractionally perform an enzyme reaction of the constituent substance in a lipoprotein, characterized in fractionally masking enzyme reactivity of the constituent substance in a specified lipoprotein by forming a complex with the specified lipoprotein.

3. In a method for fractional measurement of a constituent substance of a lipoprotein in components in biological specimens, the step to fractionally perform an enzyme reaction of the constituent substance in a lipoprotein, characterized in that the enzyme reaction is performed by fractionally masking enzyme reactivity of the constituent substance in a low density lipoprotein by forming a complex with the low density lipoprotein, while eliminating the constituent substances in a lipoprotein other than the low density lipoprotein, and then recovering and measuring the enzyme reactivity of the constituent substance in the low density lipoprotein which has been masked.

4. In a method for fractional measurement of a constituent substance of a lipoprotein in components in biological specimens, the step to fractionally perform an enzyme reaction of the constituent substance in a lipoprotein, characterized in that the enzyme reaction is performed by fractionally masking enzyme reactivity of the constituent substance in a very low density lipoprotein by forming a complex with the very low density lipoprotein, while eliminating the constituent substances in a lipoprotein other than the very low density lipoprotein, and then recovering and measuring the enzyme reactivity of the constituent substance in the very low density lipoprotein which has been masked.

5. In a method for fractional measurement of a constituent substance of a lipoprotein in components in biological specimens, the step to fractionally perform an enzyme reaction of the constituent substance in a lipoprotein by fractionally masking enzyme reactivity of a constituent substance in a lipoprotein other than the constituent substance in a high density lipoprotein by forming a complex with the lipoprotein other than the high density lipoprotein.

6. The method as claimed in any of claims 2 to 5, wherein the formation of a complex is achieved with calixarenes.

7. The method as claimed in claim 6, wherein the constituent substance in a lipoprotein in components of biological specimens is cholesterol.

8. The method as claimed in claim 7, wherein the method is a fractional measurement method of the constituent substance in a lipoprotein in components contained in biological specimens.

9. The method as claimed in claim 7, wherein the method employs a reagent for fractional measurement for the constituent substance in a lipoprotein in components contained in biological specimens.

10. A kit containing a reagent for fractional measurement of a constituent substance in a lipoprotein in components contained in biological specimens for use in the method as claimed in claim 1.

* * * * *